United States Patent [19]
Lee et al.

[11] 3,948,955
[45] Apr. 6, 1976

[54] 4'-CARBOXY-FLAVONE

[75] Inventors: Thomas Brian Lee; David Norman Hardern; John Raymond Bantick, all of Loughborough, England

[73] Assignee: Fisons Limited, London, England

[22] Filed: Nov. 11, 1974

[21] Appl. No.: 522,590

[30] Foreign Application Priority Data
Nov. 21, 1973  United Kingdom............... 54004/73

[52] U.S. Cl. ........... 260/345.2; 260/345.5; 424/283
[51] Int. Cl.² ..................................... C07D 311/02
[58] Field of Search...................... 260/345.2, 345.5

[56] References Cited
UNITED STATES PATENTS
3,720,690   3/1973   King et al. ........................ 260/345.2
3,790,580   2/1974   Johnson et al.................... 260/345.2
3,823,165   7/1974   Cairns et al....................... 260/345.2

*Primary Examiner*—James O. Thomas, Jr.
*Assistant Examiner*—Nicky Chan
*Attorney, Agent, or Firm*—Merriam, Marshall, Shapiro & Klose

[57]  ABSTRACT

There are provided compounds of the formula:

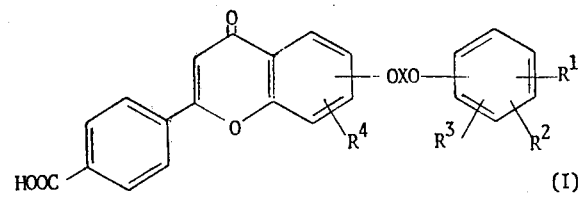

(wherein R¹, R², R³ and R⁴, which may be the same or different, each represent hydrogen, hydroxy, alkenyl, alkanoyl or alkyl, and X represents a hydrocarbon chain containing from 2 to 10 carbon atoms, optionally substituted by a hydroxy group) and pharmaceutically acceptable derivatives thereof.

The compounds are antagonists of the slow reacting substance of anaphylaxis.

12 Claims, No Drawings

4'-CARBOXY-FLAVONE

This invention concerns new compounds, processes for their preparation, and compositions containing them.

The new compounds of the present invention are those of formula I:

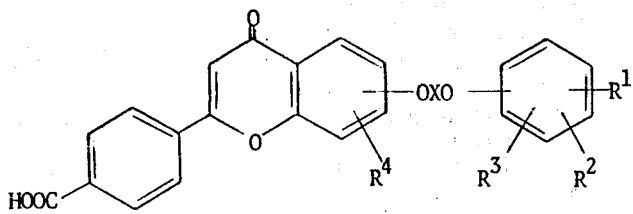

(wherein $R^1$, $R^2$, $R^3$ and $R^4$, which may be the same or different, each represent hydrogen, hydroxy, alkenyl, alkanoyl or alkyl, and X represents a hydrocarbon chain containing from 2 to 10 carbon atoms, optionally substituted by a hydroxy group), and pharmaceutically acceptable derivatives thereof.

This invention also provides a process for the preparation of a compound of formula I, or a pharmaceutically acceptable derivative thereof, which comprises: a. hydrolysing a compound of formula XIII,

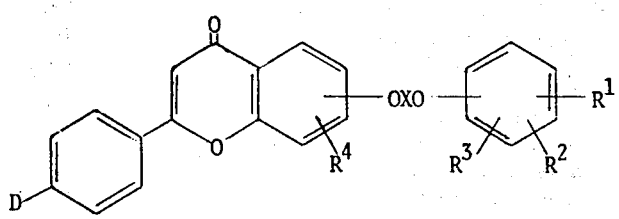

(wherein $R^1$, $R^2$, $R^3$, $R^4$ and X are as defined hereinbefore, and D represents a group hydrolysable to a carboxy group), or b. reacting a compound of formula III or an ester thereof with a compound of formula IV:

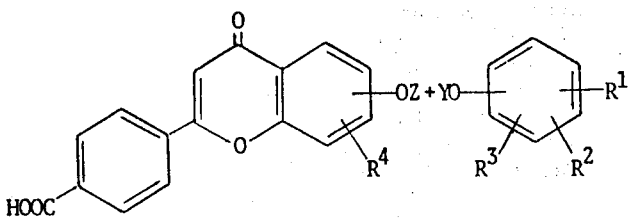

(wherein $R^1$, $R^2$, $R^3$ and $R^4$ are as defined hereinbefore, and Y and Z represent the pair of groups (i) hydrogen or a reactive metal and (ii) a hydrocarbon chain having from 2 to 10 carbon atoms and carrying an anion forming group or an epoxide group), and c. where desired or necessary, converting the resulting compound of formula I to a pharmaceutically acceptable derivative thereof or vice versa.

In process (a) the group D may, for example, be a carboxylic ester, amide or nitrile group, which may be hydrolysed to a —COOH group. The hydrolysis may be carried out using conventional techniques, for example, under mildly basic conditions, e.g., using sodium bicarbonate.

In process (b) when Y or Z is a reactive metal the metal may, for example, be an alkali metal, e.g., sodium, or another reactive metal, e.g., thallium. When Y or Z represents a hydrocarbon chain carrying an anion forming group the anion forming group may be, for example, a halogen atom, e.g., bromine, or a sulphonate group, e.g., a methyl sulphonate or a p-toluenesulphonate group. When Y or Z represents a hydrocarbon chain carrying a halogen atom the reaction may be carried out in the presence of a solvent which is inert under the reaction conditions, e.g., acetone and in the presence of an acid acceptor, e.g., potassium carbonate. The reaction is also preferably carried out under anhydrous conditions and in the presence of a suitable catalyst, e.g., KI. When Y or Z represent a hydrocarbon group carrying an epoxide group the reaction may be carried out at an elevated temperature in a solvent which is inert under the reaction conditions, e.g., dioxan or dimethylformamide, and in the presence of a suitable catalyst, e.g., trimethylbenzylammonium hydroxide. Alternatively the reaction may be carried out in the presence of a tertiary alcohol, e.g., t-butanol or 1,1-dimethyl-propan-1-ol and in the presence of the potassium salt of the alcohol as catalyst.

The compounds of formulae III and IV are either known or may be made from known starting materials in a manner known for the production of similar known compounds. Compounds of formula XIII may be made by a process analogous to process (b) above.

The compounds of formula I and, where desired or necessary, the intermediates therefor, may be recovered from the reaction mixtures in which they are produced by conventional techniques.

The compounds of formula I and their pharmaceutically acceptable derivatives, for example their pharmaceutically acceptable salts, esters and amides, e.g., their sodium, lower alkylamine, e.g., ethylamine, and hydroxy - substituted lower alkylamine, salts, are also useful because they possess pharmacological properties. In particular the compounds are antagonists of the slow-reacting substance of anaphylaxis (SRS-A), or its pathological effects, as is indicated by their activity in the test set out in Example A. The compounds also antagonise the effects of SRS-A obtained during antigen challenge of sensitised human chopped lung or isolated guinea pig ileum as described in Example A. The compounds also have the same utility at the same dosages as the compounds of Dutch Pat. No. 68,11740.

The compounds are thus of use in the treatment of disorders in which SRS-A is a factor, for example skin afflictions, hay fever and obstructive airways diseases, e.g., asthma.

The compounds of formula I and pharmaceutically acceptable derivatives thereof are also useful because they antagonise bronchospasms induced by methacholine and histamine in the guinea-pig (see the method of Konzett J and Rossler R Arch. exp. Path. Pharmak. 1940, 195 71 as modified by Burden D T and Parkes M W Br. J Pharmac 1971 41 122). The compounds are useful as bronchodilators in man.

For the above mentioned bronchospasmolytic and bronchodilator uses the dosage administered will, of course, vary with the compound employed, the mode of administration and the treatment desired. However, in general, satisfactory results are obtained when the compounds are administered at a dosage of from 0.5 to 5.0 mg per kg of animal body weight in the test set out above. For man the indicated total daily dosage is in the range of from about 20mg to 200mg which may be administered in divided doses from 2 to 3 times a day or in sustained release form. Thus unit dosage forms suitable for administration (by inhalation or by mouth) comprise from about 10mg to 100mg of the compound admixed with a solid or liquid pharmaceutically acceptable diluent, carrier or adjuvant.

For the above-mentioned anti SRS-A uses, the dosage administered will, of course, vary depending upon the compound employed, mode of administration and treatment desired. However, in general satisfactory results are obtained when administered at a daily dosage of from about 1 milligram to about 10 milligrams per kilogram of animal body weight, preferably given in divided doses 2 to 4 times a day or in sustained release form. For the larger mammals, the total daily dosage is in the range of from about 50 milligrams to about 700 milligrams, and dosage forms suitable for administration comprise from about 12 milligrams to about 350 milligrams of the compound admixed with a solid or liquid pharmaceutical carrier or diluent. The compounds may be administered during or before the attack of the disorder to be treated.

The compounds may be administered in admixture with a pharmaceutically acceptable adjuvant, diluent or carrier, the composition used depending on many factors including the disorder to be treated. The compounds may be administered parenterally, orally, by inhalation or topically.

The invention also provides a process for the preparation of a pharmaceutically acceptable salt of a compound of formula I, which process comprises treating a compound of formula I, an ester or amide thereof or another salt thereof with an appropraite base, salt by a metathetical process.

Those flavonyl compounds in which the —OXO— group is attached to the chromone nucleus in the 7 position are preferred.

It is preferred that $R^4$ is hydrogen or lower alkyl. It is also preferred that $R^4$ should be in the 6- or 8-position in the flavonyl compounds or in the 5- or 8-position and adjacent to the —OXO— chain in the xanthonyl compounds.

Preferred values of $R^1$, $R^2$, $R^3$ and $R^4$ are hydrogen, hydroxy, lower alkanoyl or lower alkyl.

Preferred compounds of formula I are those in which $R^4$ is hydrogen or propyl, $R^1$ is hydrogen or propyl, $R^2$ is hydroxy and $R^3$ is acetyl.

The group X is preferably a straight chain alkylene group containing, for example, from 2 to 7 carbon atoms and optionally sibstituted by a hydroxy group. X preferably represents a 2-hydroxytrimethylene radical.

Specific preferred compounds of this invention are: 4-[7-(4-acetyl-3-hydroxy-2-propylphenoxy)-2-hydroxypropoxy)-4-oxo-8-propyl-4H-1-benzopyran-2yl]benzoic acid, and its sodium salt, 4-[7-3-(4-acetyl-3-hydroxy-2-propylphenoxy)propoxy)-4-oxo-8-propyl-4H-1-benzopyran-2-yl]benzoic acid, and its sodium salt, In this specification and in the claims 'lower' is used to mean a group containing up to and including 6 carbon atoms.

The invention is illustrated, but in no way limited by the following Examples, in which temperatures are in °C.

EXAMPLE A

The procedure set out below is used to assess the effectiveness of a compound in antagonising SRS-A. The test makes use of the agonist (contractile) effect of SRS-A on isolated guinea-pig ileum.

A satisfactory preparation of SRS-A can be obtained from egg albumen sensitised guinea-pigs. Three weeks after sensitisation, the lungs from such guinea-pigs are removed, perfused free of blood, and chopped. Samples of washed, chopped lung are then challenged with egg albumen (antigen) solution. The supernatants collected 15 minutes after addition of antigen contain histamine and SRS-A and can be used, in the presence of an antihistamine, to induce effects due to SRS-A.

An isolated section of the terminal portion of a guinea-pig ileum is suspended in Tyrode solution, which contains atropine sulphate $10^{-6}M$ (700 μg/liter) and mepyramine maleate $10^{-6}M$ (400 μg/liter). Atropine sulphate is included to reduce the spontaneous activity of the ileum preparation and to exclude the effects of possible cholinergic agents. Mepyramine maleate is included to exclude the effects of histamine. The composition of the Tyrode solution in g/l distilled water is NaCl 8.0, KCl 0.2, $CaCl_2$ 0.2, $MgCl_2$ 0.1, $NaHCO_3$ 1.0, $NaH_2PO_4 2H_2O$ 0.05 and dextrose 1.0. A 2ml organ bath is preferred for economy of SRS-A, the tension on the tissue should be about 600 mg and the bathing temperature 37°C.

A dose of unpurified SRS-A is selected which produces similar repetitive submiximal contractions of the ileum. Each contraction is recorded for 90 seconds when the tissue is washed to allow relaxation. Five minutes is allowed between doses of SRS-A.

The compound under test is added to the organ bath 30 seconds before a dose of SRS-A. A range of concentrations of the compound is chosen to give a log concentration/inhibitory response graph. From this graph, the concentration of compound which would inhibit the ileum contraction to SRS-A by 50% ($IC_{50}$) is determined.

EXAMPLE 1

Sodium 4-[7-(3-(4-acetyl-3-hydroxy-2-propylphenoxy)-2-hydroxy-propoxy)-4-oxo-8-propyl-4H-1-benzopyran-2-yl]benzoate a. 4-(7-Hydroxy-4-oxo-8-propyl-4H-1-benzopyran-2-yl)benzoic acid To a solution of 4-methoxycarbonylbenzoyl chloride (19.85g) in dry pyridine (50 ml) was added a solution of 3-propylresacetophenone (9.7g) in dry pyridine (50 ml), and the solution stirred at room temperature for 24 hours. The mixture was poured into dilute hydrochloric acid and extracted into ethyl acetate. The organic phase was washed with dilute hydrochloric acid, sodium hydrogen carbonate solution and water, dried over magnesium sulphate and filtered. Evaporation of solvent gave a yellow oil, this oil was dissolved in dry pyridine, powdered potassium hydroxide (2.3g) was added and the mixture heated at 100°C for 1 hour. The resulting mixture was poured in dilute acetic acid and the solid collected by filtration, dried and then treated with acetic acid (100 ml) and concentrated sulphuric acid (10 ml). The mixture was heated under reflux for 1 hour and then poured into water. The solid obtained was collected by filtration and dissolved in dilute sodium hydroxide. Acidification with dilute hydrochloric acid gave a brown solid which was collected by filtration and recrystallised twice from ethanol to give 5.0g of 4-(7-hydroxy-4-oxo-8-propyl-4H-1-benzopyran-2-yl)benzoic acid as a colourless solid.

b. Ethyl 4-(7-hydroxy-4-oxo-8-propyl-4H-1-benzopyran-2-yl)benzoate

The solid acid product of step (a) (5.0g) was suspended in dry ethanol and the mixture saturated with hydrogen chloride, following which dissolution of the solid occurred. The solution was refluxed for 1 hour and evaporated to dryness. The solid obtained was dissolved in ethyl acetate, washed with sodium hydrogen carbonate solution and water, dried over magnesium sulphate, filtered and evaporated to leave a pink solid. The solid was recrystallised from aqueous ethanol to give 3.5g of ethyl 4-(7-hydroxy-4-oxo-8-propyl-4H-1-benzopyran-2-yl)benzoate, melting point 225°–6°.

Analysis Found: C, 71.6; H, 5.8; $C_{21}H_{20}O_5$ requires: C, 71.6; H, 5.7;

c. 4-(7-[3-(4-Acetyl-3-hydroxy-2-propylphenoxy)-2-hydroxy propoxy]-4-oxo-8-propyl-4H-1-benzopyran-2-yl)benzoic acid A mixture of 4-(2,3-epoxpropoxy)-2-hydroxy-3-propyl-acetophenone (2.5g) and the ester product of step (b) (3.15g) in dimethylformamide (25 ml), with 3 drops of Triton B as catalyst, was heated under reflux for 4 hours and then evaporated to yield a dark oil. The oil was dissolved in ethyl acetate and washed with 1% sodium hydroxide solution, dried over magnesium sulphate, filtered and evaporated to leave a solid. The solid was crystallised twice from ethanol to leave 3.5g of ethyl 4-(7-[3-(4-acetyl-3-hydroxy-2-propylphenoxy)-2-hydroxypropoxy]-4-oxo-8-propyl-4H-1-benzopyran-2-yl)benzoate.

This ester was hydrolysed by heating under reflux with 30 mls of 10% sodium carbonate solution and 30 mls of ethanol for one hour. The solution was acidified to give a solid which was crystallised from ethanol three times to give 1.4g of 4-(7-[3-(4-acetyl-3-hydroxy-2-propylphenoxy)-2-hydroxypropoxy]-4-oxo-8-propyl-4H-1-benzopyran-2-yl)benzoic acid, melting point 204°–206°C.

Analysis Found: C, 66.0; H, 6.1; $C_{33}H_{34}O_9$ 1½ $H_2O$ Requires: C, 65.8; H, 6.0 d. Sodium 4-(7-[3-(4-acetyl-3-hydroxy-2-propylphenoxy)-2-hydroxypropoxy]-4-oxo-8-propyl-4H-1-benzopyran-2-yl)benzoate A mixture of the acid product of step (c) (2.5g) and sodium bicarbonate (0.37g) in ethanol (200 ml) and water (50 ml) was heated on a steam bath to effect solution. The solution was evaporated to near dryness and the remaining water removed as its benzene azeotrope. The buff solid obtained was dried to give 2.6g of sodium 4-(7-[3-(4-acetyl-3-hydroxy-2-propylphenoxy)-2-hydroxypropoxy]-4-oxo-8-propyl-4H-1-benzopyran-2-yl)benzoate.

Analysis Found: C, 64.6; H, 5.8 $C_{33}H_{33}O_9Na$ $1H_2O$ Requires: C, 64.4; H, 5.7

EXAMPLE 2

Sodium 4-[7-(2-(4-acetyl-3-hydroxy-2-propylphenoxy)ethoxy)-4-oxo-8-propyl-4H-1-benzopyran-2-yl]benzoate a. 4-(2-Bromoethoxy)-2-hydroxy-3-propylacetophenone To a stirred, refluxing mixture of 2,4-dihydroxy-3-propylacetophenone (19.4g), 1,2-dibromethane (75.0g) and water (300 ml) was added slowly a solution of sodium hydroxide (4.0g) in water (60 ml) over 15 minutes. After 5 hours the mixture was cooled, and partitioned between chloroform and water. The organic phase was washed with dilute (5%) sodium hydroxide solution, and water, dried and evaporated to an oil, which was distilled at 205°–210°/11 mm to give 4-(2-bromoethoxy)-2-hydroxy-3-propylacetophenone as an oil (8.8g) which later solidified (mp 54°–58°C). The material was greater than 96% purity by glc and showed a consistant NMR spectrum, and m/e = 300/302.

b. Ethyl 4-[7-(2-(4-acetyl-3-hydroxy-2-propylphenoxy)ethoxy)-4-oxo-8-propyl-4H-1-benzopyran-2-yl]benzoate A mixture of the above-prepared bromide (6.85g), ethyl 4-(7-hydroxy-4-oxo-8-propyl-4H-1-benzopyran-2-yl)benzoate (7.3g), anhydrous potassium carbonate (3.1g), potassium iodide (0.5g) and dry acetone (200 ml) was refluxed and stirred for 24 hours, and then filtered while hot. The filtrate was evaporated to oil, which was dissolved in ethyl acetate and washed with 2% sodium hydroxide solution. Evaporation gave a solid which was crystallised from an ethanol dioxan mixture to give 5.0g of ethyl 4-[7-(2-(4-acetyl-3-hydroxy-2-propylphenoxy)ethoxy-4-oxo-8-propyl-4H-1-benzopyran-2-yl]benzoate, mp 167°–168°.

Analysis Found: C, 70.5; H, 6.4% $C_{34}H_{36}O_8$ requires: C, 71.3; H, 6.3% c. 4-[7-(2-(4-acetyl-3-hydroxy-2-propylphenoxy)ethoxy)-4-oxo-8-propyl-4H-1-benzopyran-2-yl]benzoic acid The above-prepared ester (4.5g) was dissolved in ethanol (600 ml) and 0.1N sodium hydroxide (120 ml) was added. The mixture was refluxed for 1 hour cooled, diluted with water, and acidified to give 4.0g of 4-[7-(2-(4-acetyl-3-hydroxy-2-propylphenoxy)ethoxy)-4-oxo-8-propyl-4H-1-benzopyran-2-yl]benzoic acid as a solid, mp 271°–272° (decomp). Analysis Found: C, 70.55; H, 6.2 $C_{32}H_{32}O_8$ requires: C, 70.6; H, 5.9% d. Sodium 4-[7-(2-(4-acetyl-3-hydroxy-2-propylphenoxy)ethoxy)-4-oxo-8-propyl-4H-1-benzopyran-2-yl]benzoate The above-prepared acid (4.0g) and sodium bicarbonate (0.608g) were heated at 60° in 90% ethanol until dissolution occurred. The solution was filtered and evaporated to give 3.8g of sodium 4-[7-(2-(4-acetyl-3-hydroxy-2-propylphenoxy)ethoxy)-4-oxo-8-propyl-4H-1-benzopyran-2-yl]benzoate.

EXAMPLE 3

Sodium 4-[7-(3-(4-acetyl-3-hydroxy-2-propylphenoxy)propoxy)-4-oxo-8-propyl-4H-1-benzopyran-2-yl]benzoate a. 4-(3-Bromopropoxy)-2-hydroxy-3-propylacetophenone To a mixture of 1,3-dibromopropane (80.8g), potassium carbonate (27.6g) and potassium iodide (0.5g) in dry acetone (500 ml), heated under reflux, was added 3-propylresacetophenone (38.8g) and the mixture was maintained under reflux for 24 hours.

The mixture was filtered and the solution evaporated to leave a dark oil, which was distilled to give two fractions. The fraction bp(0.2 mm) 190°–195° was collected to yield 13.0g of 4-(3-bromo-propoxy)-2-hydroxy-3-propylacetophenone which showed a consistent NMR spectrum.

b. Ethyl 4-[7-(3-(4-acetyl-3-hydroxy-2-propylphenoxy)propoxy)-4-oxo-8-propyl-4H-1-benzopyran-2-yl]benzoate A mixture of ethyl 4-(7-hydroxy-4-oxo-8-propyl-4H-1-benzopyran-2-yl)benzoate (10.6g) and the above-prepared bromide (9.9g) were condensed by the method of Example 2(b) to yield 7.0g of ethyl 4-[7-(3-(4-acetyl-3-hydroxy-2-propylphenoxy)propoxy)-4-oxo-8-propyl-4H-1-benzopyran-2-yl]benzoate hemihydrate as a solid after crystallisation from ethanol, melting point 170°–171°.

Analysis Found: C, 70.7; H, 6.6; $C_{35}H_{38}O_8 \cdot \frac{1}{2}H_2O$ requires: C, 70.6; H, 6.55;

c. 4-[7-(3-(4-acetyl-3-hydroxy-2-propylphenoxy)propoxy)-4-oxo-8-propyl-4H-1-benzopyran-2-yl]benzoic acid The above-prepared ester (5.85g) was hydrolysed by the method of Example 2 (c) to yield 3.4g of 4-[7-(3-(4-acetyl-3-hydroxy-2-propylphenoxy)propoxy)-4-oxo-8-propyl-4H-1-benzopyran-2-yl] benzoic acid, melting point 226°–228°, after crystallisation from ethyl acetate.

Analysis Found: C, 70.55; H, 6.35; $C_{33}H_{34}O_8$ requires: C, 70.95; H, 6.14;

d. Sodium 4-[7-(3-(4-acetyl-3-hydroxy-2-propylphenoxy)propoxy)-4-oxo-8-propyl-4H-1-benzopyran-2-yl]benzoate The above acid (3.54g) and sodium bicarbonate (0.533g) were reacted by the method of Example 2(d) to yield 3.5g of sodium 4-[7-(3-(4-acetyl-3-hydroxy-2-propylphenoxy)propoxy)-4-oxo-8-propyl-4H-1-benzopyran-2-yl]benzoate.

Analysis Found: C, 67.2; H, 6.2 $C_{33}H_{33}NaO_8$ requires: C, 67.6; H, 5.9

We claim:

1. A compound of the formula:

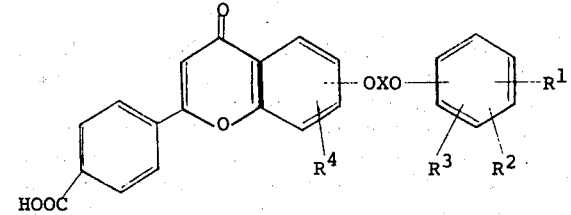

wherein $R^1$, $R^2$, $R^3$ and $R^4$, which may be the same or different, each represent hydrogen, hydroxy, lower alkanoyl, or lower alkyl, and X represents an alkylene chain containing from 2 to 10 carbon atoms, optionally substituted with a hydroxy group, or a pharmaceutically acceptable salt thereof.

2. A compound as described in claim 1 wherein at least one of $R^1$, $R^2$, $R^3$ and $R^4$ is hydrogen.

3. A compound as described in claim 1 wherein at least one of $R^1$, $R^2$, $R^3$ and $R^4$ is a hydroxy group.

4. A compound as described in claim 1 wherein at least one of $R^1$, $R^2$, $R^3$ and $R^4$ is a $C_1$ to $C_6$ alkyl group.

5. A compound as described in claim 1 wherein at least one of $R^1$, $R^2$, $R^3$ and $R^4$ is a $C_1$ to $C_6$ alkanoyl group.

6. A compound as described in claim 1 wherein X represents a $C_2$ to $C_7$ alkylene chain.

7. A compound as described in claim 1 wherein X represents a straight $C_2$ to $C_7$ alkylene chain substituted by a hydroxy group.

8. A compound as described in claim 1 which is the sodium salt.

9. A compound as described in claim 1 which is a $C_1$ to $C_6$ alkylamine salt.

10. A compound as described in claim 1 which is a hydroxy substituted $C_1$ to $C_6$ alkylamine salt.

11. A compound according to claim 1, which is selected from the group consisting of:

4-[7-(3-(4-acetyl-3-hydroxy-2-propylphenoxy)-2-hydroxypropoxy)-4-oxo-8-propyl-4H-1-benzopyran-2-yl]benzoic acid, and its sodium salt; 4-[7-(3-(4-acetyl-3-hydroxy-2-propylphenoxy)propoxy-4-oxo-8-propyl-4H-1-benzopyran-2-yl]benzoic acid, and its sodium salt; and 4-[7-(2-(4-acetyl-3-hydroxy-2-propylphenoxy)ethoxy-4-oxo-8-propyl-4H-1-benzopyran-2-yl]benzoic acid, and its sodium salt.

12. 4-[7-(3-(4-acetyl-3-hydroxy-2-propylphenoxy)-2-hydroxypropoxy)-4-oxo-8-propyl-4H-1-benzopyran-2-yl]benzoic acid, and its sodium salt.

* * * * *

UNITED STATES PATENT AND TRADEMARK OFFICE
CERTIFICATE OF CORRECTION

PATENT NO. : 3,948,955
DATED : April 6, 1976
INVENTOR(S) : Thomas Brian Lee et al.

It is certified that error appears in the above-identified patent and that said Letters Patent are hereby corrected as shown below:

Column 3, line 10, insert --Specification-- before "No.";
Column 3, line 64, "appropraite" should be --appropriate--;
and insert --e.g. a sodium base, or with an appropriate--
before the second occurrence of "salt"; column 4, line 13
"sibstituted" should be --substituted--; column 4, line 16,
insert -- (3- -- after "4-[7-"; and, column 4, line 18,
insert --(-- after "4-[7-".

Signed and Sealed this twenty-second Day of June 1976

[SEAL]

Attest:

RUTH C. MASON
*Attesting Officer*

C. MARSHALL DANN
*Commissioner of Patents and Trademarks*